(12) United States Patent
Sippy

(10) Patent No.: US 11,344,564 B1
(45) Date of Patent: May 31, 2022

(54) METHOD OF TREATMENT BASED ON REDUCED MONOAMINE OXIDASE A ACTIVITY

(71) Applicant: Lennham Pharmaceuticals, Inc., Concord, MA (US)

(72) Inventor: Bradford C. Sippy, Acton, MA (US)

(73) Assignee: Lennham Pharmaceuticals, Inc., Concord, MA (US)

(*) Notice: Subject to any disclaimer, the term of this patent is extended or adjusted under 35 U.S.C. 154(b) by 0 days.

(21) Appl. No.: 17/554,003

(22) Filed: Dec. 17, 2021

Related U.S. Application Data

(60) Provisional application No. 63/290,212, filed on Dec. 16, 2021, provisional application No. 63/282,262, filed on Nov. 23, 2021, provisional application No. 63/242,244, filed on Sep. 9, 2021, provisional application No. 63/235,482, filed on Aug. 20, 2021.

(51) Int. Cl.
*A61K 31/675* (2006.01)
*A61K 31/4045* (2006.01)

(52) U.S. Cl.
CPC ........ *A61K 31/675* (2013.01); *A61K 31/4045* (2013.01)

(58) Field of Classification Search
CPC .................................................. A61K 31/675
See application file for complete search history.

(56) References Cited

U.S. PATENT DOCUMENTS

| | | | |
|---|---|---|---|
| 10,519,175 B2 * | 12/2019 | Londesbrough | A61K 9/0053 |
| 11,000,534 B1 * | 5/2021 | Sippy | A61K 31/4045 |
| 2019/0192498 A1 | 6/2019 | Stamets | |
| 2020/0199161 A1 | 6/2020 | Londesbrough et al. | |
| 2021/0363104 A1 | 11/2021 | Nivorozhkin et al. | |

FOREIGN PATENT DOCUMENTS

WO   WO-2021/155468 A1   8/2021

OTHER PUBLICATIONS

"Psilocin-d4 Stable Isotopes," CAT No. CS-T-93519 (2020).
Barker et al., "Comparison of the brain levels of N,N-dimethyltryptamine and alpha, alpha, beta, beta-tetradeutero-N,N-dimethyltryptamine following intraperitoneal injection: The in vivo kinetic isotope effect," Biochem Pharmacol, 31(15): 2513-2516 (1982).
Blair et al., "Effect of Ring Fluorination on the Pharmacology of Hallucinogenic Tryptamines," J. Med. Chem., 43: 4701-4710 (2000).
Biei et al., "Simultaneous Production of Psilocybin and a Cocktail of b-Carboline Monoamine Oxidase Inhibitors in "Magic" Mushrooms," Chem. Eur. J., 26: 729-734 (2020).
Brown et al., "Pharmacokinetics of Escalating Doses of Oral Psilocybin in Healthy Adults," Clin Pharmacokinet, 56:1543-1554 (2017).
Dinis-Oliveira, "Metabolism of psilocybin and psilocin: clinical and forensic toxicological relevance," Drug Metabolism Reviews, 49(1):84-91 (2017).
Exempt Chemical Preparations List, Drug Enforcement Administration, Nov. 7, 2017 (284 pages).
Greenan et al., "Preparation and Characterization of Novel Crystalline Solvates and Polymorphs of Psilocybin and Identification of Solid Forms Suitable for Clinical Development," ResearchGate: 29 pages (2020).
Halpern, "Hallucinogens and dissociative agents naturally growing in the United States," Pharmacology & Therapeutics, 102: 131-138 (2004).
International Search Report and Written Opinion for International Application No. PCT/US2021/053895 dated Dec. 20, 2021.
Jann et al., "Psilocybin Revisted: The Science Behind the Drug and Its Surprising Therapeutic Potential," Psychiatric Times, 38(3): 12 pages (2021).
Kargbo et al., "Direct Phosphorylation of Psilocin Enables Optimized cGMP Kilogram-Scale Manufacture of Psilocybin," ACS Omega, 5: 16959-16966 (2020).
Magana, A Tryptamine Comeback: Interest Beyond Illicit Use, 2015, Analytix, vol. 3, Sigma-Aldrich, Psilocin-D10 solution, CAS No. 1435934-64-7, Cat. No. P-099 and P-049 (2015).
Martin et al., "The Identification of LSD-Like Hallucinogens Using the Chronic Spinal Dog," Drug and Alcohol Dependence, 3: 113-123 (1978).
Mertens et al., "Therapeutic mechanisms of psilocybin: changes in amygdala and prefrontal functional connectivity during emotional processing after psilocybin for treatment-resistant depression," J Psychopharmacol, 34(2): 167-180 (2020).
Psilocin-D10 solution, Cat No. P-099, Cas No. 1435934-64-7, p. 1-2 (2021).
Psilocin-D10, Item Details, Cerilliant Analytical Reference Standards (2020).
Psilocybin-D4, Chemical properties, CAS:1246819-43-1 (2020).
Sherwood et al., "An Improved, Practical, and Scalable Five-Step Synthesis of Psilocybin," Synthesis, 52: 688-694 (2020).
Shirota et al., "Concise Large-Scale Synthesis of Psilocin and Psilocybin, Principal Hallucinogenic Constituents of "Magic Mushroom"," J. Nat. Prodc. 66: 885-887 (2003).
STN Reg No. 1246819-43-1, entered into STN Oct. 22, 2010 (2010).
STN Reg No. 1435934-64-7, entered into STN Jun. 7, 2013 (2013).
Sugrue., "A study of the role of noradrenaline in behavioural changes produced in the rat by psychotomimetic drugs," Br. J. Pharmac. 35: 243-252 (1969).
Toronto Research Chemicals Inc Safety Data Sheet, Version 5.0 for Psilocybin-d4, prepared Aug. 21, 2013, p. 1-4 (2013).

(Continued)

*Primary Examiner* — Rei Tsang Shiao
(74) *Attorney, Agent, or Firm* — Foley Hoag LLP

(57) ABSTRACT

Provided herein are methods for the safe use of compositions comprising psilocin and prodrugs of psilocin for treating and/or preventing various diseases and conditions, such as mood or psychiatric disorders.

22 Claims, 4 Drawing Sheets

(56) References Cited

OTHER PUBLICATIONS

Tyls et al., "Psilocybin—Summary of knowledge and new perspectives," European Neuropsychopharmacology, 24: 342-356 (2014).
Vaupel et al., "The Inhibition of Food Intake In The Dog by LSD, Mescaline, Psilocin d-Amphetamine and Phenylisopropylamine Derivates," Life Sciences, 24(26): 2427-2432 (1979).

* cited by examiner

METHOD OF TREATMENT BASED ON REDUCED MONOAMINE OXIDASE A ACTIVITY

This application claims the benefit of U.S. Provisional Application Nos. 63/290,212 filed Dec. 16, 2021, U.S. Provisional Application 63/282,262 filed Nov. 23, 2021, U.S. Provisional Application 63/242,244 filed Sep. 9, 2021, and U.S. Provisional Application 63/235,482 filed Aug. 20, 2021, the contents of which are fully incorporated by reference herein.

BACKGROUND

Psilocybin is a tryptamine alkaloid, which may be isolated from various genera of fungi including the genus Psilocybe. Psilocybin is known to have hallucinogenic, anxiolytic, and psychoactive activities. In vivo, psilocybin is rapidly dephosphorylated into the active metabolite, psilocin, which activates serotonin 2A (5-HT2A) receptors in the central nervous system (CNS), mimicking the effects of serotonin.

Psilocybin- and psilocin-based compounds have been investigated as potential treatments for anxiety and depression in life-threatening diseases, depression, obsessive-compulsive disorder, alcoholism and nicotine addiction, cluster headaches and autism. However, psilocybin is considered an illegal drug in most countries and is currently a "Schedule I" substance in the United States, like heroin and LSD.

Psilocin can be metabolized in humans by both monoamine oxidase and aldehyde dehydrogenase to 4-hydroxy-indole-3-acetaldehyde, which is then further metabolized to 4-hydroxyindole-3-acetic acid and 4-hydroxytryptophole. See, e.g., Jann, "Psilocybin Revisited: The Science Behind the Drug and Its Surprising Therapeutic Potential", Psychiatric Times, Vol 38, Issue 3, Volume 03 (2021). "Whether psilocin is a MAO-A or B substrate has not been clarified . . . ". See Beck 1998, "Presence of phenylethylamine in hallucinogenic psilocybe mushroom: Possible role in adverse reactions", J Anal Toxicol 22:45-49 (1998).

It is believed that naturally-occurring monoamine oxidase inhibitors in Psilocybe mushrooms increase or enhance the pharmacological effects of psilocybin. See, e.g., Blei et al., "Simultaneous Production of Psilocybin and a Cocktail of β-Carboline Monoamine Oxidase Inhibitors in 'Magic' Mushrooms", Chemistry, 2020 January; 26(3) 729-734. For this reason, psilocybin is often consumed with MAO inhibitors to intensify the hallucinogenic effects. See, e.g., Ricardo Jorge Dinis-Oliveira, "Metabolism of psilocybin and psilocin: clinical and forensic toxicological relevance", Drug Metabolism Reviews (2017), 49:1, 84-91.

To date, the risks associated with administering a psilocybin- or psilocin-based compound to a subject having reduced monoamine oxidase activity (including, e.g., the risks associated with co-administering a psilocybin- or psilocin-based compound and a monoamine oxidase inhibitor, or arising from the concurrent use of a psilocybin- or psilocin-based compound and a monoamine oxidase inhibitor) have not been appreciated or studied. It has been surprisingly discovered that monoamine oxidase A (and not monoamine oxidase B) is responsible for the metabolism of psilocin, and that the safe administration of a psilocybin- or psilocin-based compound to a subject requires a determination of whether the subject has reduced monoamine oxidase A activity. It has also been surprisingly discovered that, if the subject is found to have reduced monoamine oxidase A activity, a psilocybin- and psilocin-based compound can nonetheless be safely and effectively administered by administration of a below-normal dose of the compound to the subject. It has also been surprisingly discovered that certain isotopically-enriched forms of psilocybin and psilocin are resistant to metabolism by monoamine oxidase A, and as a result, a normal dose of those isotopically-enriched compounds can be safely and effectively administered to a subject that has, or is determined to have, reduced monoamine oxidase A activity.

SUMMARY OF THE INVENTION

The present invention relates to methods of using compositions (e.g., pharmaceutical compositions) comprising psilocin (4-hydroxy-N,N-dimethyltryptamine) or prodrugs of psilocin such as psilocybin ([3-[2-(dimethylamino)ethyl]-1H-indol-4-yl] dihydrogen phosphate), or a pharmaceutically acceptable salt, hydrate, or solvate thereof. Psilocin and prodrugs of psilocin, or pharmaceutically acceptable salts, hydrates, and solvates thereof, and compositions comprising those compounds, which may be used in the methods described herein are further described in U.S. Pat. Nos. 10,519,175; 11,000,534; WO2021155470; WO2021155468; and WO2021234608, the disclosure of each of which is incorporated by reference herein in its entirety.

In certain embodiments, the method comprises preventing or treating a neurological or psychiatric disorder in a subject in need thereof.

In certain embodiments, the method comprises the step of determining if the subject has a monoamine oxidase A deficiency. In certain embodiments, the monoamine oxidase A deficiency is caused by use of the use of a monoamine oxidase inhibitor. In certain embodiments, the monoamine oxidase A deficiency is caused by genetic polymorphism of the monoamine oxidase A gene or monoamine oxidase A gene promoter. See, e.g., Huang et al., "An Association between a Functional Polymorphism in the Monoamine Oxidase A Gene Promoter, Impulsive Traits and Early Abuse Experiences", Neuropsychopharmacol. 29, 1498-1505 (2004). In certain embodiments, the monoamine oxidase A deficiency is caused by a genetic mutation which results in a dysfunctional monoamine oxidase A gene, including but not limited to the genetic defect that causes Brunner syndrome.

In certain embodiments, the determining step includes obtaining or having obtained a biological sample from the subject, and performing or having performed a genetic analysis (e.g. a genotyping assay) on the biological sample to determine if the subject has a genetic mutation or certain genetic polymorphism of the monoamine oxidase A gene or monoamine oxidase A gene promoter that is associated with reduced monoamine oxidase A activity.

In certain embodiments, if the subject has or is determined to have reduced monoamine oxidase A activity, the method comprises administering to the subject a below-normal dose of psilocin or a prodrug of psilocin, or pharmaceutically acceptable salt, hydrate, or solvate thereof. In certain embodiments, if the subject does not have or is determined to not have reduced monoamine oxidase A activity, the method comprises administering to the subject a normal dose of psilocin or a prodrug of psilocin, or pharmaceutically acceptable salt, hydrate, or solvate thereof. In certain embodiments, if the subject has reduced monoamine oxidase A activity, the method comprises administering to the subject a normal dose of an isotopically-enriched compound of Formula (IC) or (ID) as described in U.S. Pat. No. 11,000, 534, including a compound of Formula (IA-2) or (IA-3), the disclosure of which is incorporated by reference herein in its entirety.

The details of one or more embodiments of the present disclosure are set forth herein. Other features, objects, and advantages of the present disclosure will be apparent from the Detailed Description and Claims.

DEFINITIONS

Figure 1A:
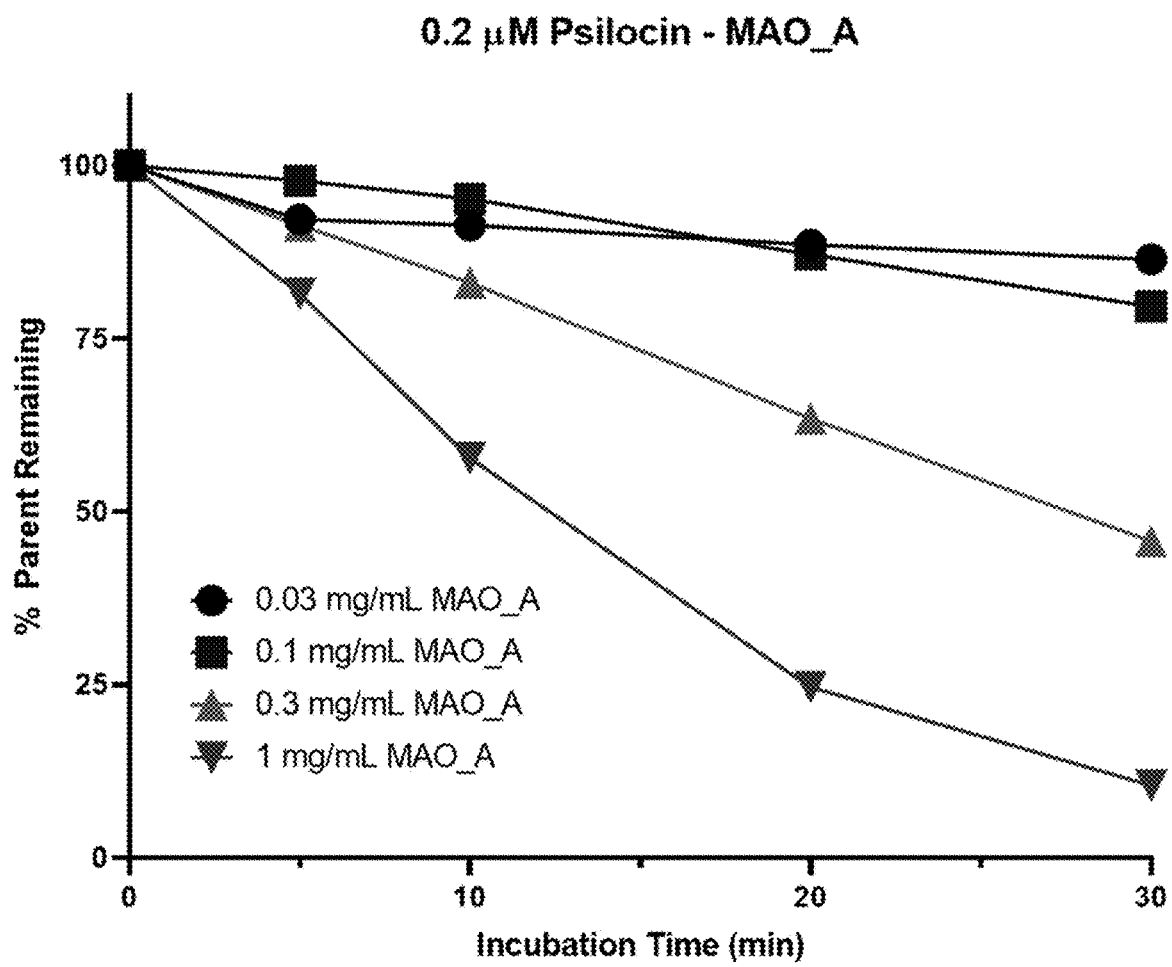
FIG. 1 shows the in vitro metabolism of psilocin by human MAO-A (FIGS. 1A & 1B) and human MAO-B (FIGS. 1C & 1D).

Before further description of the present invention, and in order that the invention may be more readily understood, certain terms are first defined and collected here for convenience.

The terms "composition" and "formulation" are used interchangeably.

The amount of an active agent or combination of active agents thereof included in a provided composition described herein will depend on the target population. In some embodiments, a provided composition contains an effective amount of an active agent. The term "effective amount," as used herein, refers to a sufficient amount of the active agent to produce a desired outcome. The exact amount required will vary from subject to subject, depending on the species, age, general condition of the subject, and the indication. The term "therapeutically effective amount" as used herein refers to a sufficient amount of a pharmaceutical agent to achieve the intended purpose, such as, for example, to cause a reduction of symptoms of a condition or disease. A "prophylactically effective amount" refers to a sufficient amount of a pharmaceutical agent to achieve the intended purpose, such as prevention of a condition or disease, one or more symptoms associated with the condition or disease, and/or the recurrence thereof. In certain embodiments, an effective amount of a composition is the effective amount of the active agent included in the composition.

The phrase "same or equivalent amount" as used herein refers to amounts as measured by mass or by moles, respectively.

The term "deuterated" refers to a compound or substituent in which one or more protium ($^1$H) atom(s) is/are replaced by one or more deuterium atom(s) and in which the abundance of deuterium at each deuterated position of the compound is higher than the natural abundance of deuterium, which is about 0.015%. The terms "is deuterium" and "are deuterium" refers to atom(s) in a compound in which one or more protium ($^1$H) atom(s) is/are replaced by one or more deuterium atom(s). A deuterated compound or substituent is considered to be "enriched for deuterium" when the abundance of deuterium at least one position is higher than the natural abundance of deuterium, which is about 0.015%. In a deuterated compound, the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

Reference to psilocin or a prodrug of psilocin, or a pharmaceutically acceptable salt, hydrate, or solvate thereof, includes all amorphous and polymorph forms. Amorphous and polymorphic forms of the compounds described herein may be prepared and characterized as set forth in U.S. Pat. No. 10,519,175, the entire disclosure of which is incorporated by reference herein. In certain aspects, reference to psilocin or a prodrug of psilocin, or a pharmaceutically acceptable salt, hydrate, or solvate thereof, includes all isotopic (deuterated) forms.

Instances of deuterium in a chemical compound provided herein may be shown through the use of the letter "D".

DETAILED DESCRIPTION OF CERTAIN EMBODIMENTS OF THE INVENTION

The present invention relates to methods of using compositions comprising psilocin or a prodrug of psilocin, or a pharmaceutically acceptable salt, hydrate, or solvate thereof, in the treatment or prevention of a disease or a condition.
Compounds and Compositions Used in the Methods Psilocin and prodrugs of psilocin, or pharmaceutically acceptable salts, hydrates, and solvates thereof, as well as isotopically-enriched forms of those compounds, which may be used in any of the methods described herein are set forth in U.S. Pat. Nos. 10,519,175; 11,000,534; WO2021155470; WO2021155468; and WO2021234608, the disclosure of each of which is incorporated by reference herein in its entirety. In certain embodiments, the methods described herein comprise administering psilocin. In certain embodiments, the psilocin is non-isotopically enriched. In certain embodiments, the methods described herein comprise administering psilocybin. In certain embodiments, the psilocybin is non-isotopically enriched. In certain embodiments, the methods described herein comprise administering a compound of the Formula (IA-2) or (IA-3) as described in U.S. Pat. No. 11,000,534, which is incorporated by reference herein. In certain embodiments, the methods describe herein comprise administering a compound of Formula (1-28) as described in WO2021155470.

Compositions comprising psilocin and prodrugs of psilocin, or pharmaceutically acceptable salts, hydrates, and solvates thereof, as well as isotopically-enriched forms of those compounds (e.g., replacing protium with deuterium), which may be used in any of the methods described herein are described in U.S. Pat. Nos. 10,519,175; 11,000,534; WO2021155470; WO2021155468; and WO2021234608, the disclosure of each of which is incorporated by reference herein in its entirety.
Methods of Use In one aspect, the present disclosure provides methods of treating a disease in a subject in need thereof comprising administering to the subject in need thereof an effective amount (e.g., therapeutically effective amount) of a compound or composition (e.g., pharmaceutical or nutraceutical composition) of the present disclosure.

In another aspect, the present disclosure provides methods of preventing a disease in a subject in need thereof comprising administering to the subject in need thereof an effective amount (e.g., therapeutically effective amount) of a compound or composition (e.g., pharmaceutical or nutraceutical composition) of the present disclosure.

In certain embodiments, the subject is an animal. The animal may be of either sex and may be at any stage of development. In certain embodiments, the subject described herein is a human. The human may be a child or an adult. In certain embodiments, the subject is a human of age 2 or less. In certain embodiments, the subject is a human of age 2 to 17. In certain embodiments, the subject is a human of age 18 to 65. In certain embodiments, the subject is older than 65 years of age. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a dog. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice, transgenic pigs). In certain embodiments, a subject in need thereof is a subject in need of delivery of an active agent or a composition, a subject in need of treatment of a disease, or a subject in need of prevention of a disease. The terms "subject" and "patient" are used interchangeably herein. In certain embodiments, the subject has a monoamine oxidase A deficiency.

In certain embodiments, the effective amount is effective in treating the disease. In certain embodiments, the effective amount is effective in preventing the disease.

In certain aspects, the disease is a neurological disease. In certain embodiments, the disease is a neurological disease. The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including Alzheimer's disease, Parkinson's disease, amyotrophic lateral sclerosis, tauopathies (including frontotemporal dementia), and Huntington's disease. Examples of neurological diseases include headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIAD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; fibromyalgia; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; ministrokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofiaromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissiale spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

In certain embodiments, the disease is a painful condition. A "painful condition" includes neuropathic pain (e.g., peripheral neuropathic pain), central pain, deafferentation pain, chronic pain (e.g., chronic nociceptive pain, and other forms of chronic pain such as post-operative pain, e.g., pain arising after hip, knee, or other replacement surgery), fibromyalgia pain, pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the disease is a psychiatric disorder. The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D. C. (1994). Psychiatric disorders include anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders including substance abuse (e.g., alcohol dependence, amphetamine dependence, *cannabis* dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

In certain embodiments, the method further comprises administering to the subject in need thereof an additional therapy. In certain embodiments, the additional therapy is an additional pharmaceutical agent. In certain embodiments, the additional therapy is an additional nutraceutical agent. The pharmaceutical and nutraceutical compositions of the present disclosure and the additional therapy may show synergy in the methods and uses of the present disclosure.

In another aspect, the invention is directed to a method for treating a depressive disorder in a subject in need thereof, the method comprising administering to the subject a composition comprising psilocin or a prodrug of psilocin, or a pharmaceutically acceptable salt, hydrate, or solvate thereof, as described herein. In certain embodiments, the depressive disorder is major depressive disorder or treatment-resistant depression.

In another aspect, the invention is directed to a method for treating a mood disorder in a subject in need thereof, the method comprising administering to the subject a composition comprising psilocin or a prodrug of psilocin, or a pharmaceutically acceptable salt, hydrate, or solvate thereof, as described herein. In certain embodiments, the mood disorder is psychological distress (e.g., depression or anxiety) related with a life-threatening disease.

In another aspect, the invention is directed to a method for treating an anxiety disorder in a subject in need thereof, the method comprising administering to the subject a composition comprising psilocin or a prodrug of psilocin, or a pharmaceutically acceptable salt, hydrate, or solvate thereof, as described herein.

In another aspect, the invention is directed to a method for treating an addiction disorder in a subject in need thereof, the method comprising administering to the subject a composition comprising psilocin or a prodrug of psilocin, or a pharmaceutically acceptable salt, hydrate, or solvate thereof, as described herein.

In another aspect, the invention is directed to a method for treating a pain disorder in a subject in need thereof, the method comprising administering to the subject a composition comprising psilocin or a prodrug of psilocin, or a pharmaceutically acceptable salt, hydrate, or solvate thereof, as described herein.

In another aspect, the pain disorder is migraine, arthritis, headache, back pain, bursitis, chronic pain, acute pain, musculoskeletal pain, osteoarthritis, psoriatic arthritis, rheumatoid arthritis, sciatica or fibromyalgia. In another aspect, the pain disorder is migraine. In another aspect, the pain disorder is arthritis. In another aspect, the pain disorder is headache. In another aspect, the pain disorder is back pain. In another aspect, the pain disorder is bursitis. In another aspect, the pain disorder is chronic pain. In another aspect, the pain disorder is acute pain. In another aspect, the pain disorder is musculoskeletal pain. In another aspect, the pain disorder is osteoarthritis. In another aspect, the pain disorder is psoriatic arthritis. In another aspect, the pain disorder is rheumatoid arthritis. In another aspect, the pain disorder is sciatica. In another aspect, the pain disorder is migraine or headache. In another aspect, the pain disorder is fibromyalgia.

In another aspect, the invention is directed to a method for treating a psychiatric disorder in a subject in need thereof, the method comprising administering to the subject a composition comprising psilocin or a prodrug of psilocin, or a pharmaceutically acceptable salt, hydrate, or solvate thereof, as described herein.

In another aspect, the neurological or psychiatric disorder is narcolepsy, Alzheimer's disease, attention deficit hyperactivity disorder (ADHD), schizophrenia, Parkinson's disease, or depression. In another aspect, the neurological or psychiatric disorder is narcolepsy. In another aspect, the neurological or psychiatric disorder is Alzheimer's disease. In another aspect, the neurological or psychiatric disorder is attention deficit hyperactivity disorder (ADHD). In another aspect, the neurological or psychiatric disorder is schizophrenia. In another aspect, the neurological or psychiatric disorder is Parkinson's disease. In another aspect, the neurological or psychiatric disorder is depression.

In another aspect, in any of the methods described herein, the method comprises administering a single dose of a pharmaceutical composition comprising psilocin or a prodrug of psilocin, or a pharmaceutically acceptable salt, hydrate, or solvate thereof, as described herein. In another aspect, in any of the methods described herein, the method comprises administering a pharmaceutical composition a composition comprising psilocin or a prodrug of psilocin, or a pharmaceutically acceptable salt, hydrate, or solvate thereof, as described herein in the presence of supportive care, e.g. a healthcare provider, to ensure safe use of the product, to provide emotional support for the subject, and/or to monitor for possible side effects.

Reduced monoamine oxidase A activity in a subject may result from, for example, a monoamine oxidase A deficiency or exposure to a monoamine oxidase inhibitor.

In certain embodiments, the subject has a monoamine oxidase A deficiency and the method comprises administering a below-normal dose of the psilocin or a prodrug of psilocin, or a pharmaceutically acceptable salt, hydrate, or solvate thereof, as described herein. In certain embodiments, the psilocin or prodrug of psilocin, or pharmaceutically acceptable salt, hydrate, or solvate thereof, that is to be administered is not isotopically-enriched. In certain embodiments, the psilocin or prodrug of psilocin, or pharmaceutically acceptable salt, hydrate, or solvate thereof, that is to be administered is isotopically-enriched.

In any of the methods described herein, the method may comprise the step of determining if the subject has a monoamine oxidase A deficiency. In certain embodiments, the method comprises determining if the subject has a monoamine oxidase A deficiency prior to the administration of a composition comprising psilocin or a prodrug of psilocin, or a pharmaceutically acceptable salt, hydrate, or solvate thereof, as described herein. In certain embodiments, the psilocin or prodrug of psilocin, or pharmaceutically acceptable salt, hydrate, or solvate thereof, that is to be administered is not isotopically-enriched.

In certain embodiments, the monoamine oxidase A deficiency is caused by or results from the use of a monoamine oxidase inhibitor. Examples of monoamine oxidase inhibitors includes, but is not limited to, isocarboxazid (Marplan); phenelzine (Nardil); selegiline (Emsam); and tranylcypromine (Parnate). Further examples of monoamine oxidase inhibitors include drugs which are not used to treat depression but are known to inhibit monoamine oxidase, including linezolid (Zyvox); methylene blue (Provayblue); procarbazine (Matulane): rasagiline (Azilect); and selegiline (Eldepryl, Zelapar).

In certain embodiments, the monoamine oxidase A deficiency is caused by genetic polymorphism of the monoamine oxidase A gene or monoamine oxidase A gene promoter. See, e.g., Huang et al., "An Association between a Functional Polymorphism in the Monoamine Oxidase A Gene Promoter, Impulsive Traits and Early Abuse Experiences", Neuropsychopharmacol. 29, 1498-1505 (2004). In certain embodiments, the monoamine oxidase A deficiency is caused by a genetic mutation which results in a dysfunctional monoamine oxidase A gene, such the genetic defect that causes Brunner syndrome.

In certain embodiments, the determining step includes determining whether the subject has been exposed to a monoamine oxidase inhibitor. In certain embodiments, the determining step includes interviewing the subject to determine if the subject is using or has used (e.g. within the past 1, 3, 5, 7, 10 or 14 days) a monoamine oxidase inhibitor.

In certain embodiments, the determining step includes determining whether the subject has a genetic factor that is associated with reduced monoamine oxidase A activity. In certain embodiments, the determining step includes obtaining or having obtained a biological sample from the subject, and performing or having performed a genetic analysis (e.g. a genotyping assay) on the biological sample to determine if the subject has a genetic mutation or certain genetic polymorphism of the monoamine oxidase A gene or monoamine oxidase A gene promoter that is associated with reduced monoamine oxidase A activity.

In certain embodiments, the determining step includes analyzing information received from the subject to identify if the subject has reduced monoamine oxidase A activity. In certain embodiments, the determining step includes analyzing information derived from a biological sample of the subject to identify if the subject has reduced monoamine oxidase A activity.

In certain embodiments, if the subject is determined to have reduced monoamine oxidase A activity, the method comprises administering to the subject a below-normal dose of the psilocin or prodrug of psilocin, or a pharmaceutically acceptable salt, hydrate, or solvate thereof. In certain embodiments, the psilocin or prodrug of psilocin, or a pharmaceutically acceptable salt, hydrate, or solvate thereof, is not isotopically-enriched.

In certain embodiments, if the subject is determined not to have reduced monoamine oxidase A activity, the method comprises administering to the subject a normal dose of the psilocin or prodrug of psilocin, or a pharmaceutically acceptable salt, hydrate, or solvate thereof.

In certain embodiments, if the subject is determined to have reduced monoamine oxidase A activity due to the use of a monoamine oxidase inhibitor, the method comprises instructing the subject to avoid the concomitant use of the monoamine oxidase inhibitor and then administering a normal dose of the psilocin or prodrug of psilocin, or a pharmaceutically acceptable salt, hydrate, or solvate thereof. In certain embodiments, if the subject is determined to have reduced monoamine oxidase A activity due to the use of a monoamine oxidase inhibitor, the method comprises administering a normal dose of the psilocin or prodrug of psilocin, or a pharmaceutically acceptable salt, hydrate, or solvate thereof, wherein the normal dose is administered without the co-administration of, or concurrent use of, the monoamine oxidase inhibitor. In certain embodiments, the method comprises administering a normal dose of the psilocin or prodrug of psilocin, or a pharmaceutically acceptable salt, hydrate, or solvate thereof after the subject has been instructed to avoid the concomitant use of the monoamine oxidase inhibitor.

In certain embodiments, the normal dose of an active agent as provided herein is defined as, with respect to a subject and a disease or condition, the amount of the agent that has been approved as safe and effective by the United States Food and Drug Administration for administration in the subject in a particular dosage form for preventing or treating the disease or condition. In certain embodiments, the normal dose of an active agent varies by the age, gender and/or weight of the subject. In certain embodiments, the normal dose of a composition for oral administration (e.g. a tablet or solution) comprises or provides at least about 0.01 mg, 0.05 mg, 0.1 mg, 0.5 mg, 1 mg, 5 mg, 10 mg, 12.5 mg, 15 mg, 17.5 mg, 20 mg, 25 mg, 30 mg, 35 mg, 40 mg, 45 mg, or 50 mg of the psilocin or prodrug of psilocin, or pharmaceutically acceptable salt, hydrate, or solvate thereof. In certain embodiments, the normal dose of a composition for oral administration (e.g. a tablet or solution) comprises or provides 0.01 mg, 0.05 mg, 0.1 mg, 0.5 mg, 1 mg, 5 mg, 10 mg, 12.5 mg, 15 mg, 17.5 mg, 20 mg, 25 mg, 30 mg, 35 mg, 40 mg, 45 mg, or 50 mg of the psilocin or prodrug of psilocin, or pharmaceutically acceptable salt, hydrate, or solvate thereof. In certain embodiments, the normal dose of a composition for oral administration comprises or provides between 0.01 mg-0.05 mg, 0.05 mg-0.1 mg, 0.1 mg-0.5 mg, 0.5 mg-5 mg, 5 mg-10 mg, 10 mg-15 mg, 15 mg-20 mg, 20 mg-25 mg, 25 mg-30 mg, 30 mg-35 mg, 35 mg-40 mg, 40 mg-45 mg, or 45 mg-50 mg of the psilocin or prodrug of psilocin, or pharmaceutically acceptable salt, hydrate, or solvate thereof.

In certain embodiments, in any of the methods described herein, the dose of psilocin or prodrug of psilocin, or a pharmaceutically acceptable salt, hydrate, or solvate thereof is selected based on one or more of the following criteria: a monoamine oxidase A deficiency; age; gender; weight; the specific disease or condition being treated; the severity of the disease or condition; or prior use or experience with psilocin or prodrug of psilocin, or a pharmaceutically acceptable salt, hydrate, or solvate thereof.

In certain embodiments, the below-normal dose of the psilocin or prodrug of psilocin, or a pharmaceutically acceptable salt, hydrate, or solvate thereof, comprises at least 10%, 20%, 25%, 30%, 40% or 50% less of the psilocin or prodrug of psilocin, or a pharmaceutically acceptable salt, hydrate, or solvate thereof, than the normal dose. In certain embodiments, the below-normal dose of the psilocin or prodrug of psilocin, or a pharmaceutically acceptable salt, hydrate, or solvate thereof, comprises at least 5-10%, 10-20%, 20-25%, 25-30%, 30-40% or 40-50% less of the psilocin or prodrug of psilocin, or a pharmaceutically acceptable salt, hydrate, or solvate thereof, than the normal dose.

In certain embodiments, if the subject is determined to have reduced monoamine oxidase A activity, the method comprises administering to the subject a normal dose of a compound comprising isotopically-enriched psilocin or a prodrug of psilocin, or a pharmaceutically acceptable salt, hydrate, or solvate thereof. In certain embodiments, the isotopically-enriched psilocin or prodrug of psilocin comprises a compound of Formula (IC) or (ID) as described in U.S. Pat. No. 11,000,534, including a compound of Formula (IA-2) or (IA-3), which is incorporated by reference herein in its entirety. In certain embodiments, the isotopically-enriched psilocin or prodrug of psilocin comprises a compound of Formula (1-28) as described in WO2021155470.

In certain embodiments, if the subject is determined to have reduced monoamine oxidase A activity, the method comprises administering to the subject a below-normal dose of a compound comprising isotopically-enriched psilocin or a prodrug of psilocin, or a pharmaceutically acceptable salt, hydrate, or solvate thereof. In certain embodiments, the below-normal dose of an isotopically-enriched psilocin or prodrug of psilocin is higher (when taking into account differences in molecular weight) than a normal dose of a non-isotopically enriched compound having the same structure.

In certain embodiments, the method reduces the risk of one or more side effects associated with the administration of psilocin or a prodrug of psilocin, or a pharmaceutically acceptable salt, hydrate, or solvate thereof. In one aspect, the side effect is derealization, visual alteration and distortion, such as halos of light and vivid colors, dilated pupils, dizziness, drowsiness, impaired concentration, muscle weakness, lack of coordination, unusual body sensations, nausea, paranoia, confusion, hallucinations, nausea or vomiting, yawning, headache, fatigue, suicidal behavior, intentional self-injury, or suicidal ideation. In another aspect, the side effect is increased blood pressure (systolic and diastolic) or increased heart rate.

In certain embodiments, the method comprises monitoring the subject for suicidal behavior, intentional self-injury, or suicidal ideation after administration of the psilocin or prodrug of psilocin. In certain embodiments, the method comprises monitoring the subject for suicidal behavior, intentional self-injury, and suicidal ideation after administration of the psilocin or prodrug of psilocin.

In another aspect, the method achieves a lower or comparable relative magnitude of exposure of psilocin in plasma, the gastrointestinal tract, and/or the central nervous system (including the brain) in a subject having reduced monoamine oxidase A activity when compared to the administration of the same dose of the same compound (e.g., psilocin or a prodrug of psilocin, or a pharmaceutically acceptable salt, hydrate, or solvate thereof) to a subject not having reduced monoamine oxidase A activity.

In certain embodiments, the method comprises providing a pharmaceutical composition comprising psilocin or a prodrug of psilocin, or a pharmaceutically acceptable salt, hydrate, or solvate thereof, with a label comprising prescribing instructions. In certain embodiments, the prescribing instructions instruct a healthcare provider or subject to avoid the concomitant use of monoamine oxidase A inhibitors. In certain embodiments, the prescribing instructions instruct a healthcare provider to administer a below-normal dose of the psilocin structure or a prodrug of psilocin, or a pharmaceutically acceptable salt, hydrate, or solvate thereof to a subject that has reduced monoamine oxidase A activity (e.g. due to the concomitant use of a monoamine oxidase A inhibitor).

Example 1

A study was conducted to assess the metabolism of psilocin by human MAO-A and MAO-B under the conditions set forth in Table 1.

TABLE 1

| Study species | Human |
|---|---|
| Incubation volume | 300 µl, pH 7.4 in phosphate buffer with 2 mM $MgCl_2$ |
| Protein content | 0.03, 0.1, 0.3 and 1 mg/ml |
| Cofactors & concentrations | No cofactors |
| Preincubation time | 2 min @ 37° C. |
| Incubation times | 0, 5, 10, 20 and 30 min |
| Replicates | 2 |
| Reaction started by | Addition of study compound |
| Termination of incubations | 2-fold volume of 75% acetonitrile |
| Storage of the samples | −20° C. until analysis |
| Test compound concentration | 0.2 and 2 µM |

Figure 1B:
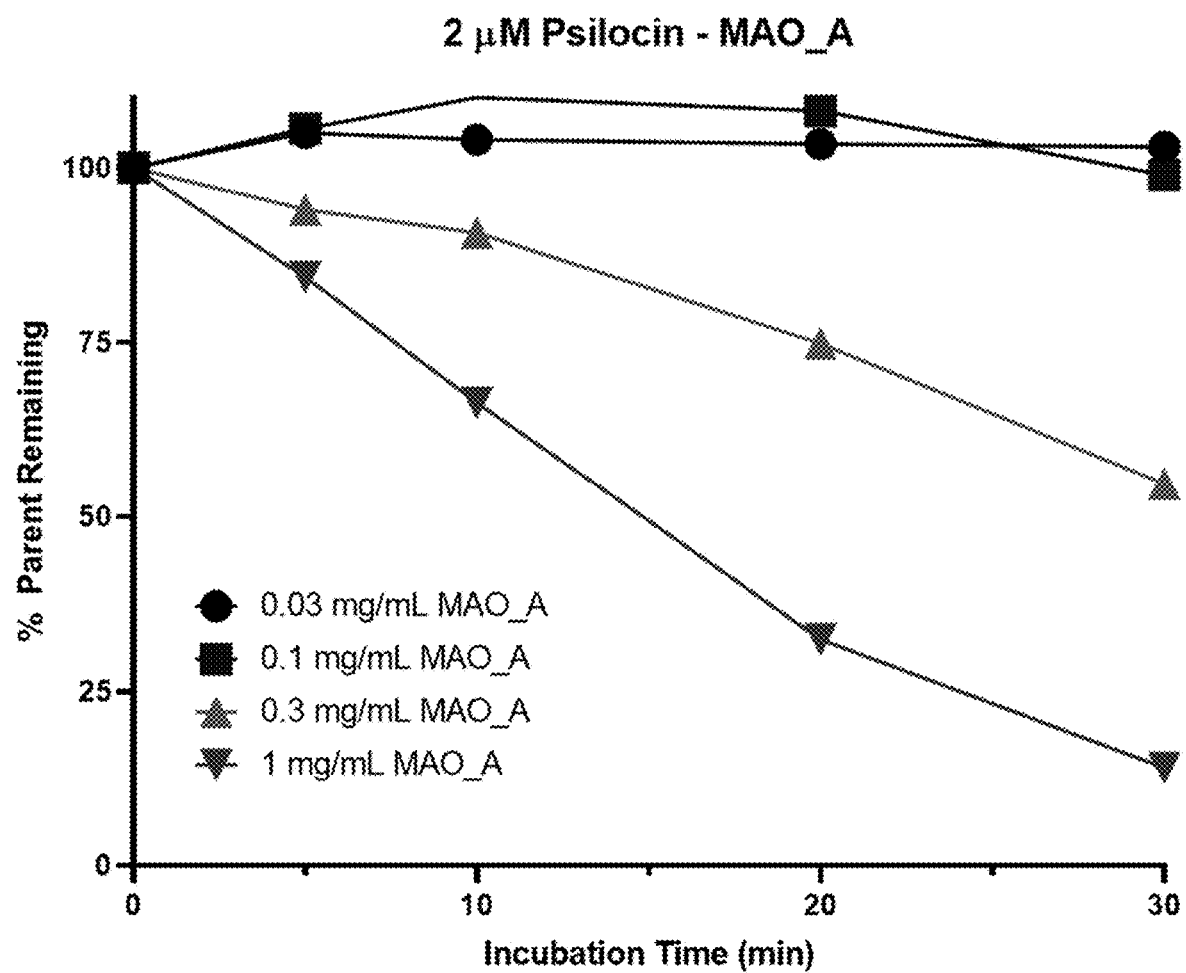
Figure 1C:
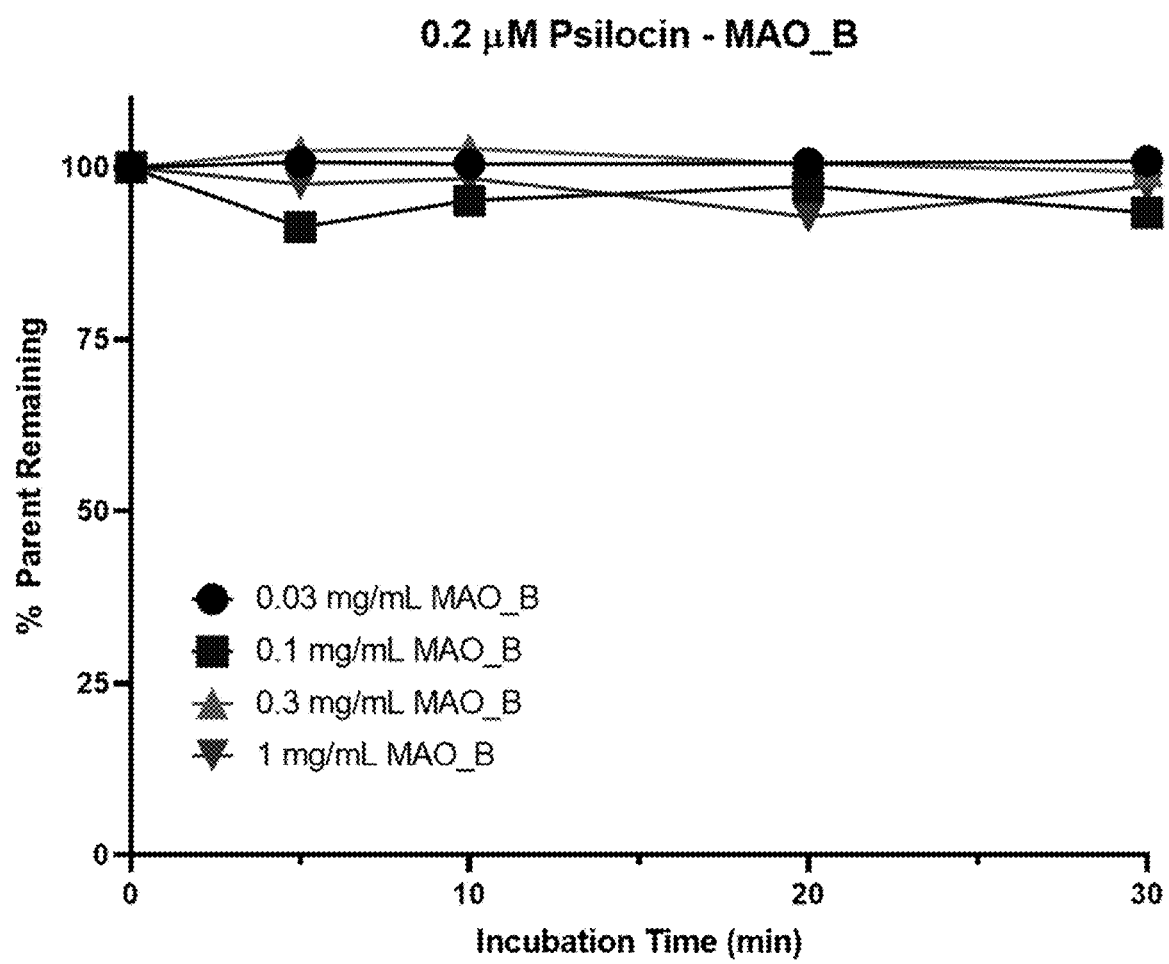
Figure 1D:
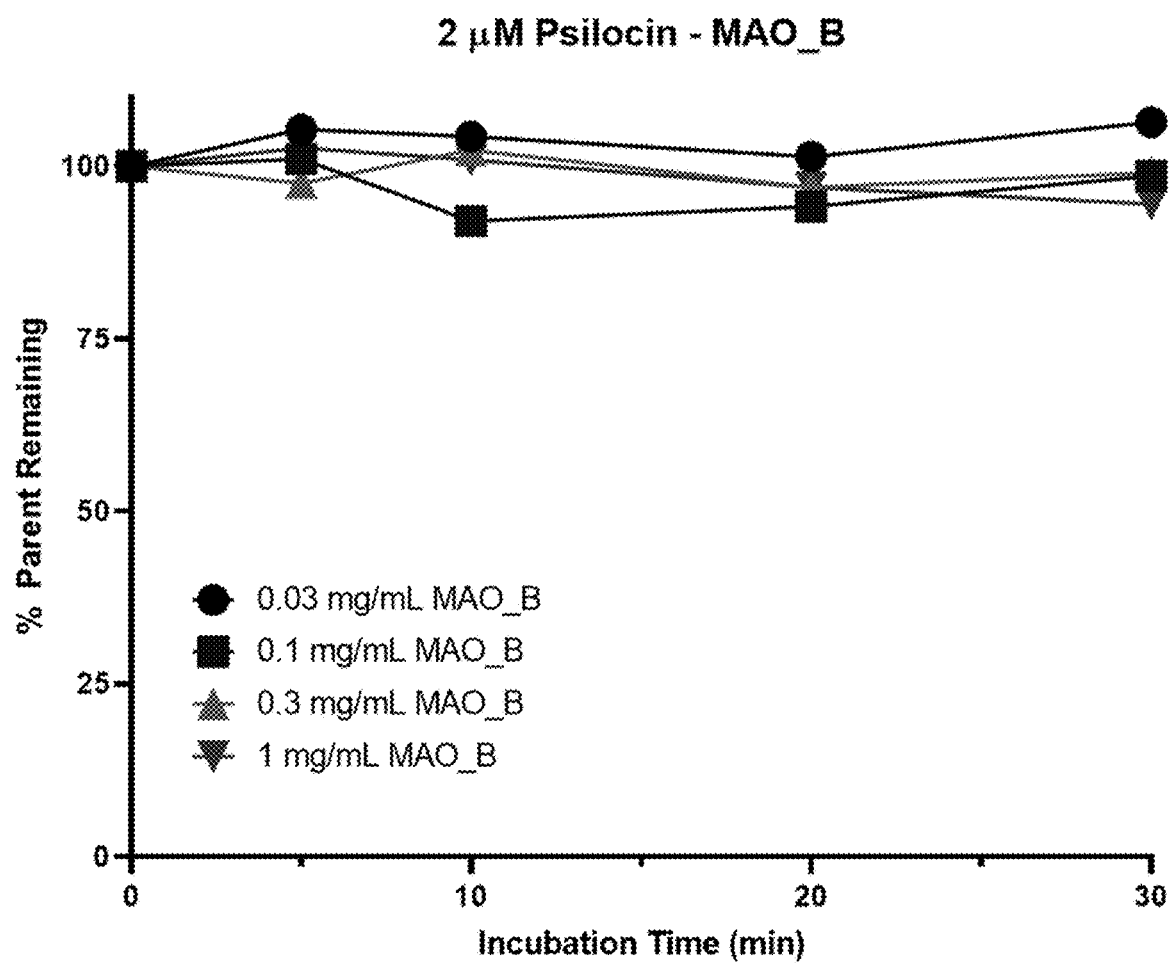

The results show that psilocin is metabolized by human MAO-A (FIGS. 1A & 1B), but not human MAO-B (FIGS. 1C & 1D) under the study conditions. The study conditions and results are further described in co-pending U.S. Provisional Application No. 63/223,305, which is incorporated herein by reference.

Various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising," "including," and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a neurological or psychiatric disorder in a subject in need thereof with psilocin or psilocybin, or a pharmaceutically acceptable salt, hydrate, or solvate thereof, the method comprising:
determining whether the subject has reduced monoamine oxidase A activity; if the subject has reduced monoamine oxidase A activity, administering to the subject a below-normal dose of the psilocin or psilocybin, or pharmaceutically acceptable salt, hydrate, or solvate thereof.

2. The method of claim 1, wherein the normal dose of the psilocin or psilocybin is at least about 25 mg.

3. The method of claim 1, wherein the normal dose of the psilocin or psilocybin is at least about 10 mg.

4. The method of claim 1, wherein the normal dose of the psilocin or psilocybin is at least about 1 mg.

5. The method of claim 1, wherein the below-normal dose is at least about 10% lower than the normal dose.

6. The method of claim 1, wherein the below-normal dose is at least about 25% lower than the normal dose.

7. The method of claim 1, wherein the below-normal dose is at least about 50% lower than the normal dose.

8. The method of claim 1, wherein the psychiatric disorder is a depressive disorder or an eating disorder.

9. The method of claim 8, wherein the depressive disorder is major depressive disorder or treatment-resistant depression.

10. The method of claim 1, wherein the disorder is a neurological disorder.

11. The method of claim 10, wherein the neurological disorder is a pain disorder.

12. The method of claim 1, wherein the method comprises administering psilocin, or a pharmaceutically acceptable salt thereof, to the subject.

13. The method of claim 1, wherein the method comprises administering a psilocybin, or a pharmaceutically acceptable salt thereof, to the subject.

14. The method of claim 1, wherein the method comprises administering a pharmaceutical composition comprising the below-normal dose of the psilocin or psilocybin, or pharmaceutically acceptable salt, hydrate, or solvate thereof.

15. The method of claim 1, wherein the reduced monoamine oxidase A activity is caused by exposure of the subject to a monoamine oxidase inhibitor.

16. The method of claim 1, wherein the method comprises determining whether the subject has been exposed to a monoamine oxidase inhibitor.

17. The method of claim 16, wherein the method comprises interviewing the subject to determine whether the subject is has been exposed to a monoamine oxidase inhibitor.

18. The method of claim 1, wherein the reduced monoamine oxidase A activity is caused by a genetic factor that is associated with reduced monoamine oxidase A activity.

19. The method of claim 18, wherein the method comprises determining whether the subject has a genetic factor that is associated with reduced monoamine oxidase A activity.

20. The method of claim 19, wherein the method comprises obtaining a biological sample from the subject, and conducting a genetic analysis on the biological sample to determine if the subject has a genetic mutation or genetic polymorphism of the monoamine oxidase A gene or monoamine oxidase A gene promoter that is associated with reduced monoamine oxidase A activity.

21. The method of claim 1, wherein after administration of the psilocin or psilocybin, the subject is monitored for suicidal behavior, intentional self-injury, or suicidal ideation.

22. The method of claim 21, wherein after administration of the psilocin or psilocybin, the subject is monitored for suicidal behavior, intentional self-injury, and suicidal ideation.

* * * * *